(12) United States Patent
Behrends et al.

(10) Patent No.: US 6,258,370 B1
(45) Date of Patent: Jul. 10, 2001

(54) COMPOSITIONS FOR DISINFECTION OF SKIN AND MUCOUS MEMBRANE

(75) Inventors: Sabine Behrends, Pinneberg; Hans-Peter Harke, Hamburg, both of (DE)

(73) Assignee: Air Liquide Sante (International), Paris (FR)

( * ) Notice: Subject to any disclaimer, the term of this patent is extended or adjusted under 35 U.S.C. 154(b) by 0 days.

(21) Appl. No.: 09/297,503

(22) PCT Filed: Oct. 28, 1997

(86) PCT No.: PCT/EP97/06041

§ 371 Date: Jun. 8, 1999

§ 102(e) Date: Jun. 8, 1999

(87) PCT Pub. No.: WO98/20094

PCT Pub. Date: May 14, 1998

(30) Foreign Application Priority Data

Nov. 4, 1996 (DE) ............................................ 196 467 594

(51) Int. Cl.$^7$ ............................ A01N 25/00; A01N 25/34
(52) U.S. Cl. ............................................ 424/405; 424/404
(58) Field of Search ...................................... 424/404, 405

(56) References Cited

U.S. PATENT DOCUMENTS

| | | | |
|---|---|---|---|
| 4,454,060 | * | 6/1984 | Lat et al. ............................ 252/547 |
| 4,540,605 | * | 9/1985 | Barone et al. ........................ 427/243 |
| 4,542,125 | * | 9/1985 | Gorman et al. ........................ 514/57 |
| 4,704,404 | * | 11/1987 | Sanderson ............................ 514/568 |
| 4,975,217 | * | 12/1990 | Brown-Skrobot et al. .......... 514/574 |
| 5,767,054 | * | 6/1998 | Sprugel et al. ..................... 510/383 |

FOREIGN PATENT DOCUMENTS

| | | |
|---|---|---|
| 20 20 967 | 11/1971 | (DE) . |
| 20 20 968 | 11/1971 | (DE) . |
| 43 33 385 | 4/1995 | (DE) . |

OTHER PUBLICATIONS

C. Conrad, "Hygienic Disinfection of the Hands", *Deutsche Krankenpflegezeitschrift*, vol. 46, Jul. 1993, pp. 495–497.

* cited by examiner

*Primary Examiner*—Thurman K. Page
*Assistant Examiner*—Amy E. Pulliam
(74) *Attorney, Agent, or Firm*—Young & Thompson

(57) ABSTRACT

A process and compositions for disinfecting the skin, hands and mucous membrane. The compositions contain an optical brightener and exhibit intense fluorescence in the visible wavelength range on exposure to UV light and thus permit simple monitoring of the treated skin or mucous membrane surfaces for ensuring complete disinfection, but without exhibiting the disadvantages associated with the use of conventional dyes, such as discoloration of the skin and articles.

15 Claims, No Drawings

COMPOSITIONS FOR DISINFECTION OF SKIN AND MUCOUS MEMBRANE

CROSS REFERENCE TO RELATED APPLICATION

This is the 35 USC 371 national stage of international application PCT/EP97/06041 filed on Oct. 28, 1997, which designated the United States of America.

FIELD OF INVENTION

The invention relates to compositions, containing optical brighteners, such as compositions for disinfecting the hands, skin and mucous membrane.

BACKGROUND OF THE INVENTION

Before operations, the skin or mucous membrane in the region of the operation area is treated with antiseptic disinfectants. Here, it is necessary to ensure complete wetting of the epithelium in order to guarantee complete disinfection. For this reason, intensely coloured preparations which permit visual monitoring of the application of the disinfectant are usually used for disinfecting the skin and mucous membrane.

However, the disadvantage of these compositions is that colour changes of the skin which may occur during the operation, such as, for example, pallor as a result of depletion of blood or a blue colour due to inadequate oxygen saturation of the blood, for example in cardiac insufficiency or pulmonary diseases, are masked by the dye, and any necessary measures on the part of the surgeon are thus delayed or even completely prevented. In addition, the pronounced adhesion of the dyes to the skin, in particular of patients, is found to be very troublesome. Moreover, clothing, operating tables, floors, equipment, etc. soiled by the dyes used are difficult to clean.

SUMMARY OF THE INVENTION

It is the object of the present invention to provide a process for disinfecting a surface which do not have the abovementioned disadvantages by the application of a composition on said surface or mucous membrane surface, in order to be able to ensure complete disinfection of the operating area.

This object is achieved by compositions which contain at least one optical brightener provided that the composition does not contain any fluoro-aliphatic surfactant nor reducing agent selected from the class of hydrazine and hydroxylamine and alkali metal salts of oxygen acids of divalent sulfur and tetravalent sulfur.

Optical brighteners are compounds which are caused to fluoresce in the visible wavelength range by ultraviolet radiation, i.e. substances which absorb ultraviolet radiation and emit longer-wavelength, visible radiation.

Preferably used optical brighteners are the same substances which are also used in detergents for brightening the laundry or in various personal hygiene preparations for increasing the brilliance of, for example, soaps and cosmetic formulations. Particularly preferred optical brighteners are stilbene compounds, such as, for example, diaminostilbenedisulphonic acid, coumarin derivatives, such as, for example, 4-methyl-7-diethylaminocoumarin, 1,3-diaryldipyrazoline derivatives, such as, for example, 1,3-diphenyl-4-methyl-5-alkylpyrazoline, naphthalimide derivatives, such as, for example, N-methyl-4-methoxynaphthalimide, and benzoxazole derivatives, such as, for example, 1,2-bis(5-methylbenzoxazol-2-yl)ethylene. Pyrazoline derivatives (e.g. Hostalux® PN, from Hoechst), cationic benzimidazole derivatives (e.g. Blankophor® ACR, from Bayer) and anionic distearylbiphenyl derivatives (e.g. Blankophor® VPSP 20006, from Bayer) are very particularly preferred.

Particularly suitable are of course those optical brighteners which are used for brightening wool, such as, for example, Blankophor® ACR and Blankophor® VPSP, since this natural fibre has considerable similarity with human skin. However, brighteners for other fibres, such as, for example, polyamide, paper, polyester, polyacrylonitrile and cotton, are also suitable.

The use of optical brighteners permits the preparation of disinfectants which contain a substantially lower dye concentration and preferably no customary dyes at all. In contrast to the conventional, intensely coloured disinfectants, they are therefore also suitable for disinfecting the hands as well as equipment and work surfaces, providing for the first time a possibility for monitoring the completeness of wetting in these areas too.

The excitation wavelength for the disinfectants according to the invention depends on the optical brightener used and is preferably in the range of customary UV lamps, i.e. preferably in the range from about 300 to 400 nm.

Skin surfaces treated with the disinfectants according to the invention therefore fluoresce brightly on exposure to a UV lamp, permitting simple monitoring of the surfaces treated with the compositions and hence guaranteeing complete disinfection of the desired surface. In normal daylight, the disinfectants according to the invention and hence also the treated skin areas and all other articles, such as clothing, floors and equipment, which have come into contact with the compositions are not coloured.

A particular advantage of the optical brighteners used according to the invention is that, in contrast to many traditional dyes, they are not absorbed, therefore do not have systemic activity and are hence toxicologically safe. Furthermore, they have no sensitizing properties.

The optical brighteners are used in an amount such that, on exposure to UV light of a suitable wavelength, a clear distinction between treated and untreated surfaces is possible. For this purpose, the brighteners are typically used in an amount of from 0.0001 to 3% by weight, preferably in an amount of from 0.001 to 2.0% by weight, based on the total amount of disinfectant.

The concentration of the brightener furthermore depends on the intended use of the composition. While washing hand disinfectants frequently require higher concentrations, for example in the range from 0.2 to 1.0% by weight, since these compositions are for the most part rinsed off again after use, lower concentrations of from 0.005 to 0.5% by weight and in particular from 0.05 to 0.3% by weight may be entirely sufficient in the case of other compositions.

The disinfectants according to the invention contain, as further components, conventional constituents such as antimicrobial active ingredients, liquid carriers and excipients. Suitable compositions are known from the prior art.

Antimicrobial active ingredients include, quaternary compounds, guanidine derivatives, phenol derivatives iodine-eliminating compounds, aromatics alcohols, aliphatic alcohols, peroxide compounds such as hydrogene peroxide or organic peroxyacid compounds such as peracetic acid.

Excipients include anionic surfactants, cationic surfactants or non-ionic surfactants such as alkylether sulfates, alkylbenzene sulfonates, alkylsulfates, fatty acid esters, fattyacid alcohols, polyalkoxylated derivatives of fatty alcohols or of fatty acids, alkylpolyglycosides, betaines, sultaine, imidazoline and their derivatives, and fatty quaternary amonium salts.

Excipients also include thickening agents.

Compositions for disinfecting the skin and mucous membrane preferably contain one or more of the following constituents:

| Antimicrobial active ingredients | |
| --- | --- |
| Quaternary compounds | from 0.005 to 50% by weight; |
| Guanidine derivatives | from 0.1 to 10% by weight; |
| Phenol derivatives | from 0.02 to 5% by weight; |
| Iodine-eliminating compounds | from 0.5 to 20% by weight; |
| Peroxide compounds | from 0.001 to 10% by weight; |
| Aromatic alcohols | from 0.5 to 5% by weight |
| and/or | |
| Alcohols | from 1 to 15% by weight. |

Excipients

Surfactants (preferably cocamidopropylbetaine, sulphosuccinate, sodium lauryl ether sulphate) and/or Stabilizers (preferably $H_2O_2$, buffer substances).

Compositions for disinfecting the skin preferably contain one or more of the following constituents:

| Antimicrobial active ingredients | |
| --- | --- |
| Alcohols | from 5 to 96% by weight; |
| Quartenary compounds | from 0.05 to 50% by weight; |
| Guanidine derivatives | from 0.1 to 10% by weight; |
| Phenol derivatives | from 0.01 to 10% by weight; |
| Iodine-eliminating compounds | from 0.5 to 20% by weight; |
| Peroxide compounds | from 0.001 to 10% by weight; |
| Aromatic alcohols | from 0.5 to 10% by weight; |
| Fatty acids | from 0.1% to 5% by weight |
| and/or | |
| Hydroxy carboxylic acids | from 0.1 to 5% by weight. |

Excipients

Stabilizers (preferably $H_2O_2$).

Compositions for disinfecting the hands preferably contain one or more of the following constituents:

| Antimicrobial active ingredients | |
| --- | --- |
| Alcohols | from 5 to 96% by weight; |
| Quaternary compounds | from 0.05 to 50% by weight; |
| Guanidine derivatives | from 0.1 to 10% by weight; |
| Phenol derivatives | from 0.01 to 10% by weight; |
| Peroxide compounds | from 0.001 to 10% by weight; |
| Aromatic alcohols | from 0.5 to 10% by weight; |
| Fatty acids | from 0.1 to 5% by weight |
| and/or | |
| Hydroxy carboxylic acids | from 0.1 to 5% by weight. |

Excipients

Superfatting agents (preferably triglycerides, fatty alcohols, fatty acids),

Humectants (preferably sorbitol solution, 1,2-propylene glycol, PEG derivatives, sodium lactate)

Thickeners (preferably hydroxyethylcellulose, hydroxypropyl-cellulose, xanthans, polyacrylates)

Perfume and/or

Dyes.

Washing hand disinfectants preferably contain one or more of the following constituents:

| Antimicrobial active ingredients | |
| --- | --- |
| Alcohols | from 5 to 30% by weight; |
| Quaternary compounds | from 0.1 to 20% by weight; |
| Guanidine derivatives | from 0.1 to 10% by weight; |
| Phenol derivatives | from 0.5 to 5% by weight; |
| Iodine-eliminating compounds | from 0.5 to 20% by weight; |
| Peroxide compounds | from 0.001 to 10% by weight |
| and/or | |
| Aromatic alcohols | from 0.5 to 10% by weight. |

Excipients

Surfactants (preferably cocamidopropylbetaine, sulphosuccinate, sodium lauryl ether sulphate)

Stabilizers (preferably $H_2O_2$)

Thickeners (preferably hydroxyethylcellulose)

Dyes and/or

Perfume.

Preferred antimicrobial active ingredients are:

| | |
| --- | --- |
| Quaternary compounds: | Octenidine dihydrochloride, benzalkonium chloride; |
| Guanidine derivatives: | Chlorhexidine dihydrochloride; chlorhexidine digluconate; |
| Phenol derivatives: | 2-Biphenylol; |
| Iodine-eliminating compounds: | Polyvinylpyrrolidone-iodine (PVP-iodine); |
| Peroxide compounds: | $H_2O_2$; |
| Aromatic alcohols: | Phenoxyethanol, phenethyl alcohol, |

|  |  |
|---|---|
| Alcohols: | benzyl alcohol; Ethanol, 1-propanol, 2-propanol; |
| Hydroxycarboxylic acids: | Lactic acid; |
| Fatty acids: | Undecylenic acid. |

Compositions as herebefore described, are also an object of the present invention.

DETAILED DESCRIPTION OF THE INVENTION

The invention is illustrated in more detail below with reference to embodiments.

EXAMPLES

Example 1

Composition for Disinfecting the Skin and Mucous Membrane

A composition containing the following constituents is prepared as the composition for disinfecting the skin and mucous membrane:

| | |
|---|---|
| Octenidine dihydrochloride | 0.10% by weight |
| Phenoxyethanol | 2.00% by weight |
| Blankophor ® ACR | 0.2% by weight |
| Cocamidopropylbetaine solution 30% | 2.00% by weight |
| Sodium gluconate | 1.00% by weight |
| Water to make up to | 100% |

Phenoxyethanol is initially introduced into a first vessel and octenidine dihydrochloride is dissolved therein. In a second vessel, sodium gluconate is added to water and stirred until the sodium gluconate has completely dissolved. Thereafter, the cocamidopropylbetaine solution is added and stirred in. The two solutions are then combined and are stirred until a clear solution is obtained. Finally, Hostalux® PN liquid is added and stirring is carried out again until a clear solution is obtained.

Example 2

Composition for Disinfecting the Hands

A composition containing the following constituents is prepared as the composition for disinfecting the hands:

| | |
|---|---|
| Ethyl alcohol | 80.00% by weight |
| Isopropyl myristate | 1.00% by weight |
| Sorbitol solution | 0.50% by weight |
| Hostalux ® PN liquid (dispersion of a pyrazoline derivative) | 0.1% by weight |
| Perfume | 0.05% by weight |
| Water to make up to | 100% |

Ethanol and water are mixed, sorbitol solution is added and stirring is carried out. Thereafter, isopropyl myristate and perfume are added and the mixture is stirred until a clear solution is obtained. Hostalux® PN liquid is then added and stirring is carried out again until a clear solution is obtained.

Example 3

Composition for Disinfecting the Skin

A composition containing the following constituents is prepared as the composition for disinfecting the skin:

| | |
|---|---|
| Isopropyl alcohol | 45.00% by weight |
| 1-Propanol | 10.00% by weight |
| Hostalux ® PN liquid (dispersion of a pyrazoline derivative) | 0.1% by weight |
| Water to make up to | 100% |

Isopropyl alcohol, 1-propanol and water are mixed, Hostalux® PN liquid is added and stirring is carried out until a clear solution is obtained.

Example 4

Washing Hand Disinfectant

A composition containing the following constituents is prepared as the washing composition for disinfecting the hands:

| | |
|---|---|
| 1-Propanol | 10.00% by weight |
| Isopropyl alcohol | 8.00% by weight |
| 2-Biphenylol | 2.00% by weight |
| Cocamidopropylbetaine solution 30% | 20.00% by weight |
| Hostalux ® PN liquid (dispersion of a pyrazoline derivative) | 0.50% by weight |
| Perfume | 0.20% by weight |
| Hydroxyethylcellulose | 1.00% by weight |
| Water to make up to | 100% |

Isopropyl alcohol and 1-propanol are mixed, and the hydroxyethylcellulose is added with stirring. Thereafter, water is added to the mixture and 2-biphenylol, cocamidopropylbetaine solution and perfume are stirred into the mixture in the stated order. Hostalux® PN liquid is then added and stirring is carried out until a clear solution is obtained.

All mixtures show intense fluorescence on exposure to UV light having a wavelength of 366 nm (UV lamp: CAMAG Reprostar II or DESAGA Heidelberg UVIS universal unit).

What is claimed is:

1. Process for disinfecting a skin surface or mucous surface, which comprises applying to the surface an effective amount of a disinfecting composition which contains at least an optical brightener and optionally a humectant selected from the group consisting of sorbitol solution, 1-2 propylene glycol, PEG derivatives and sodium lactate, provided that said composition does not contain any fluoroaliphatic surfactant nor reducing agent selected from the class of hydrazine and hydroxylamine and alkali metal salts of oxygen acids of divalent sulfur and tetravalent sulfur.

2. The process according to claim 1, wherein the optical brightener is selected from the group consisting of stilbene compounds, coumarin derivatives, 1-3-diarylpyrazoline derivatives, naphthalimide derivatives, and benzoxazole derivatives.

3. The process according to claim 2, wherein the optical brightener is selected from the group consisting of diaminostilbenedisulfonic acid, 4-methyl-7-diethyl aminocoumarin, 1,3-diphenyl-4-methyl-5-alkylpyrazoline, and 1,2-bis(5-methylbenzoxazol-2-yl)ethylene.

4. The process according to claim 1, wherein the composition further contains one or more antimicrobial active ingredients selected from the group consisting of quaternary compounds, guanidine derivatives, iodine eliminating compounds, peroxide compounds, aromatic alcohols, non-aromatic alcohols, fatty acids, hydroxy carboxylic acids, phenol derivatives, and organic peroxyacid compounds.

5. The process according to claim 1, wherein the composition further contains one or more excipients selected from the group consisting of surfactants, humectants, thickeners, perfumes, and superfatting agents.

6. The process according to claim 1, wherein the composition further contains one or more stabilizers.

7. The process according to claim 4, wherein the composition contains between 0.1 and 1% by weight of octenidine dihydrochloride.

8. The process according to claim 1, wherein the surface to be disinfected is the surface of hands.

9. The process according to claim 1, wherein the composition contains from 0.0001% to 3.0% by weight of optical brightener.

10. The process according to claim 9, wherein the composition contains from 0.001 to 2% by weight of optical brightener.

11. A disinfecting composition for disinfecting a skin surface or mucous surface, which comprises at least 0.0001% to 3.0% by weight of an optical brightener and optionally a humectant selected from the group consisting of sorbitol solution, 1-2 propylene glycol, PEG derivatives and sodium lactate, provided that said composition does not contain any fluoroaliphatic surfactant nor reduction agent selected from the class of hydrazine and hydroxylamine and alkali metal salts of oxygen acids of divalent sulfur and tetravalent sulfur.

12. The composition according to claim 11, wherein the composition contains from 0.001% to 2.0% by weight of the optical brightener.

13. The composition according to claim 11, wherein the optical brightener is selected from the group consisting of stilbene compounds, coumarin derivatives, 1-3-diarylpyrazoline derivatives, naphthalimide derivatives, and benzoxazole derivatives.

14. The composition according to claim 11, wherein the composition further contains one or more antimicrobial active ingredients selected from the group consisting of quaternary compounds, guanidine derivatives, iodine eliminating compounds, peroxide compounds, aromatic alcohols, non-aromatic alcohols, fatty acids, hydroxy carboxylic acids, phenol derivatives, and organic peroxyacid compounds.

15. The composition according to claim 11, wherein the composition further contains one or more excipients selected from the group consisting of surfactants, humectants, thickeners, perfumes, and superfatting agents.

* * * * *